(12) United States Patent
Ewing et al.

(10) Patent No.: US 9,109,980 B2
(45) Date of Patent: Aug. 18, 2015

(54) SYSTEMS AND METHODS FOR AUTOMATED COLLECTION OF ANALYTES

(75) Inventors: Kenneth J. Ewing, Edgewater, MD (US); Danielle N. Dickinson, Odenton, MD (US); Robert Milloy, Baltimore, MD (US); Michael R. Bracken, West Friendship, MD (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 407 days.

(21) Appl. No.: 13/806,456

(22) PCT Filed: Jul. 1, 2011

(86) PCT No.: PCT/US2011/042778
§ 371 (c)(1),
(2), (4) Date: Mar. 12, 2013

(87) PCT Pub. No.: WO2012/003434
PCT Pub. Date: Jan. 5, 2012

(65) Prior Publication Data
US 2013/0213148 A1      Aug. 22, 2013

Related U.S. Application Data

(60) Provisional application No. 61/360,588, filed on Jul. 1, 2010.

(51) Int. Cl.
*G01N 1/22* (2006.01)
*G01N 35/00* (2006.01)

(52) U.S. Cl.
CPC .............. *G01N 1/22* (2013.01); *G01N 1/2214* (2013.01); *G01N 2035/00089* (2013.01); *G01N 2035/00108* (2013.01)

(58) Field of Classification Search
CPC . G01N 1/28; G01N 1/2214; G01N 2201/222; G01N 2001/2285
USPC ........................................................ 73/864.33
See application file for complete search history.

(56) References Cited

U.S. PATENT DOCUMENTS

| | | | | |
|---|---|---|---|---|
| 5,404,762 A | * | 4/1995 | Rodgers et al. | 73/863.25 |
| 6,833,110 B2 | | 12/2004 | Black | |
| 7,997,119 B2 | * | 8/2011 | Wu | 73/31.03 |
| 2008/0067358 A1 | * | 3/2008 | Musselman | 250/290 |
| 2008/0094804 A1 | | 4/2008 | Reynolds et al. | |
| 2008/0250877 A1 | * | 10/2008 | Wu | 73/864.33 |
| 2009/0054813 A1 | | 2/2009 | Freeman et al. | |
| 2009/0317916 A1 | | 12/2009 | Ewing et al. | |

OTHER PUBLICATIONS

International Search Report for corresponding PCT/US2011/042778, completed Oct. 25, 2011.

* cited by examiner

*Primary Examiner* — Peter Machhiarolo
*Assistant Examiner* — Nathaniel Kolb
(74) *Attorney, Agent, or Firm* — Tarolli, Sundheim, Covell & Tummino LLP

(57) ABSTRACT

One embodiment of the invention includes an automated system for collecting analyte. The system comprises a screen supply cartridge for holding a stack of clean tabs including sorbent coated screens (SCS) residing in SCS channels. The stack of tabs are arranged such that SCS tabs directly above and/or below a given SCS tab include SCS channels offset from the SCS channel of the given tab to isolate the SCS channels from one another and the environment. The system includes an air source that provides an analyte to be adsorbed by an SCS channel of a respective tab at a sampling region and a linear actuator that moves a given clean tab into the sampling region for exposing the SCS channel of the given clean tab to the analyte and providing a given exposed tab.

20 Claims, 6 Drawing Sheets

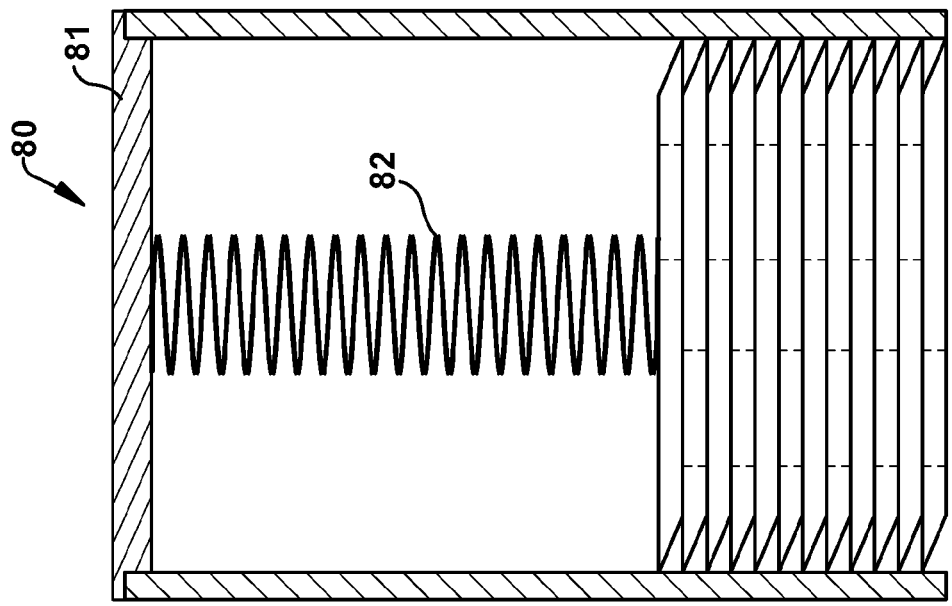
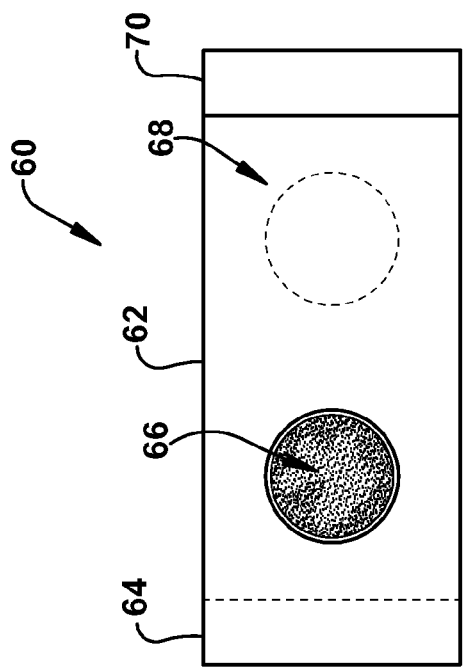
Fig. 5
Fig. 4

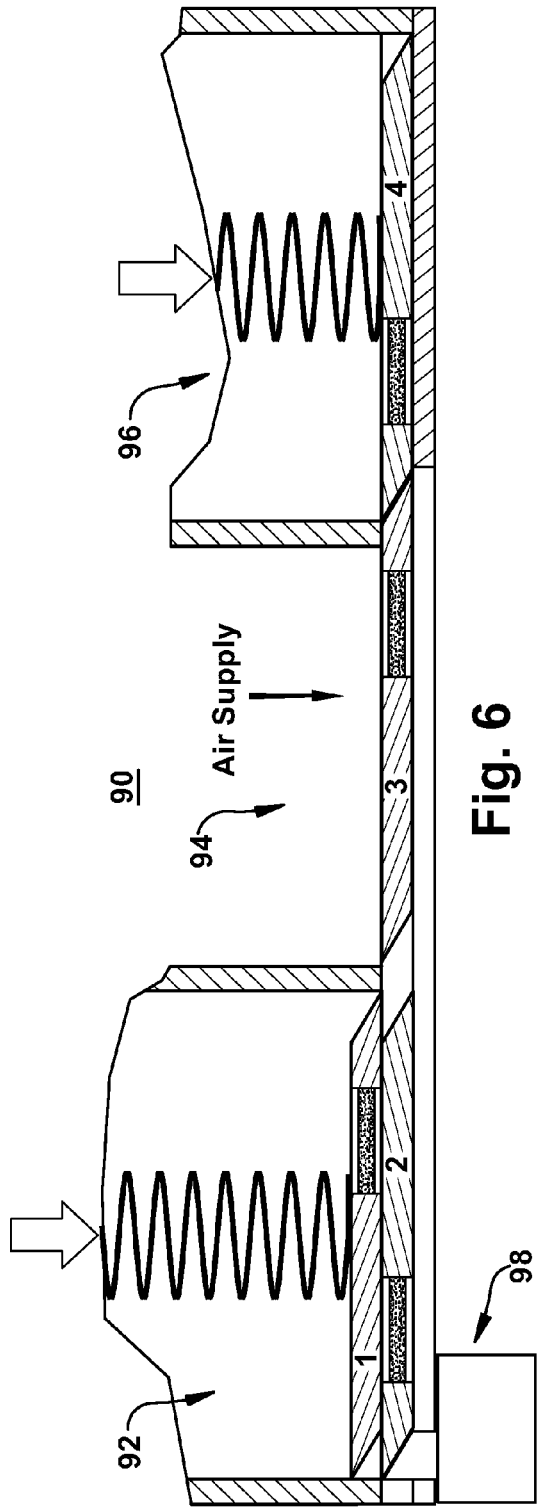
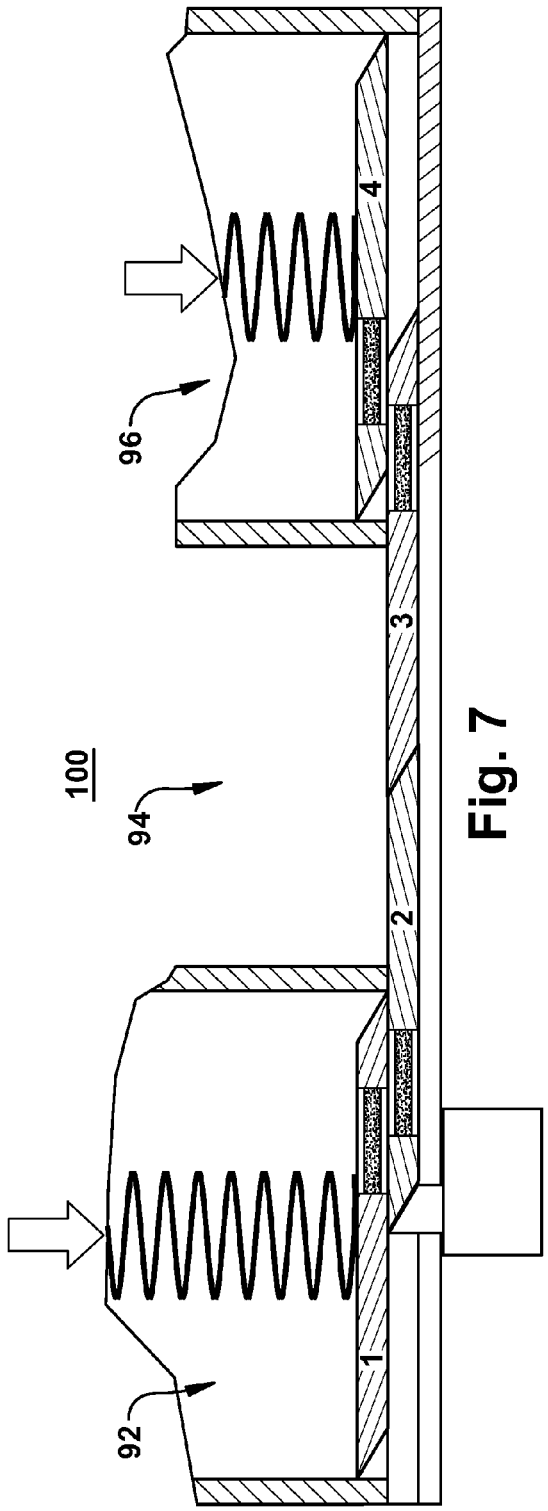

SYSTEMS AND METHODS FOR AUTOMATED COLLECTION OF ANALYTES

RELATED APPLICATIONS

This application is a 371 Patent Application Serial No. PCT/US2011/042778, filed 1 Jul. 2011, which is incorporated herein in its entirety.

TECHNICAL FIELD

The present invention relates generally to collection systems, and specifically to systems and methods for automated collection of analytes.

BACKGROUND

The collection and analysis of vapor phase analytes is employed in many environments and applications. One technique for the collection and analysis of analytes is to utilize tubes (metal or glass) that are filled with a packed bed of sorbent material of moderate to low surface area to trap a narrow range of vapor phase analytes. These sorbent tubes exhibit relatively high pressure drops due to the length of the tube and therefore require a relatively strong pump or air source to allow for the capture of a sample of analyte to provide an adequate amount of vapor phase analyte to be trapped in the sorbent material. This can be problematic when employing a mobile collection device that has limited power. To desorb the analyte trapped in the sorbent material for subsequent analysis, the tube needs be heated to a sufficient temperature for a sufficient amount of time. Due to the packed bed geometry, high temperatures and longer desorption times are necessary to efficiently desorb the trapped analyte.

In certain types of analytes, the high temperatures can cause destruction of some or all of the analyte resulting in inaccurate and inefficient analysis of the sample of analyte. Furthermore, it is cumbersome and time consuming to collect multiple samples since it requires manual switching of individual tubes after each sample and/or analysis. A diffusive sampler does not require pumps but is slow in sample collection and is constantly exposed to the environment such that not useful spatial and temporal data with respect to target analytes can be achieved.

SUMMARY

In accordance with an aspect of the invention, an automated system is provided for collecting analytes. The system comprises a screen supply cartridge for holding a stack of clean tabs including sorbent coated screens (SCS) residing in SCS channels. The stack of tabs are arranged such that SCS tabs directly above and below a given SCS tab include SCS channels offset from the SCS channel of the given tab to isolate the SCS channels from one another and the environment. The system includes an air source that provides an analyte to be adsorbed by an SCS channel of a respective tab at a sampling region and a linear actuator (e.g., linear motor) that moves a given clean tab into the sampling region for exposing the SCS channel of the given clean tab to the analyte and providing a given exposed tab.

In an aspect of the invention, the linear actuator moves the given exposed tab into a post sampling cartridge. Each of the tabs have beveled ends, such that the beveled end of an exposed tab pushes a prior exposed tab up or down the post sampling cartridge to create a stack of exposed tabs in the post sampling cartridge arranged such that SCS tabs directly above and/or below a given SCS tab include SCS channels offset from the SCS channel of the given SCS tab to isolate the SCS channels from one another and the environment.

In another aspect of the invention, the linear actuator moves the given exposed tab back into the screen supply cartridge. Each of the tabs have beveled ends, such that the beveled end of an exposed tab pushes a prior exposed tab and/or clean tab up or down the screen supply cartridge to create a stack of exposed tabs arranged such that SCS tabs directly above and/or below a given SCS tab include SCS channels offset from the SCS channel of the given SCS tab to isolate the SCS channels from one another and the environment.

BRIEF DESCRIPTION OF THE DRAWINGS

FIG. 4 illustrates a top view of an SCS tab in accordance with an aspect of the invention.

FIG. 5 illustrates a schematic diagram of SCS tabs arranged in a cartridge in a stacked channel offset configuration in accordance with an aspect of the invention.

FIG. 6 illustrates operation of the SCS autosampler during a first stage of operation in accordance with an aspect of the present invention.

FIG. 7 illustrates operation of the SCS autosampler during a second stage of operation in accordance with an aspect of the present invention.

DETAILED DESCRIPTION

Figure 1:
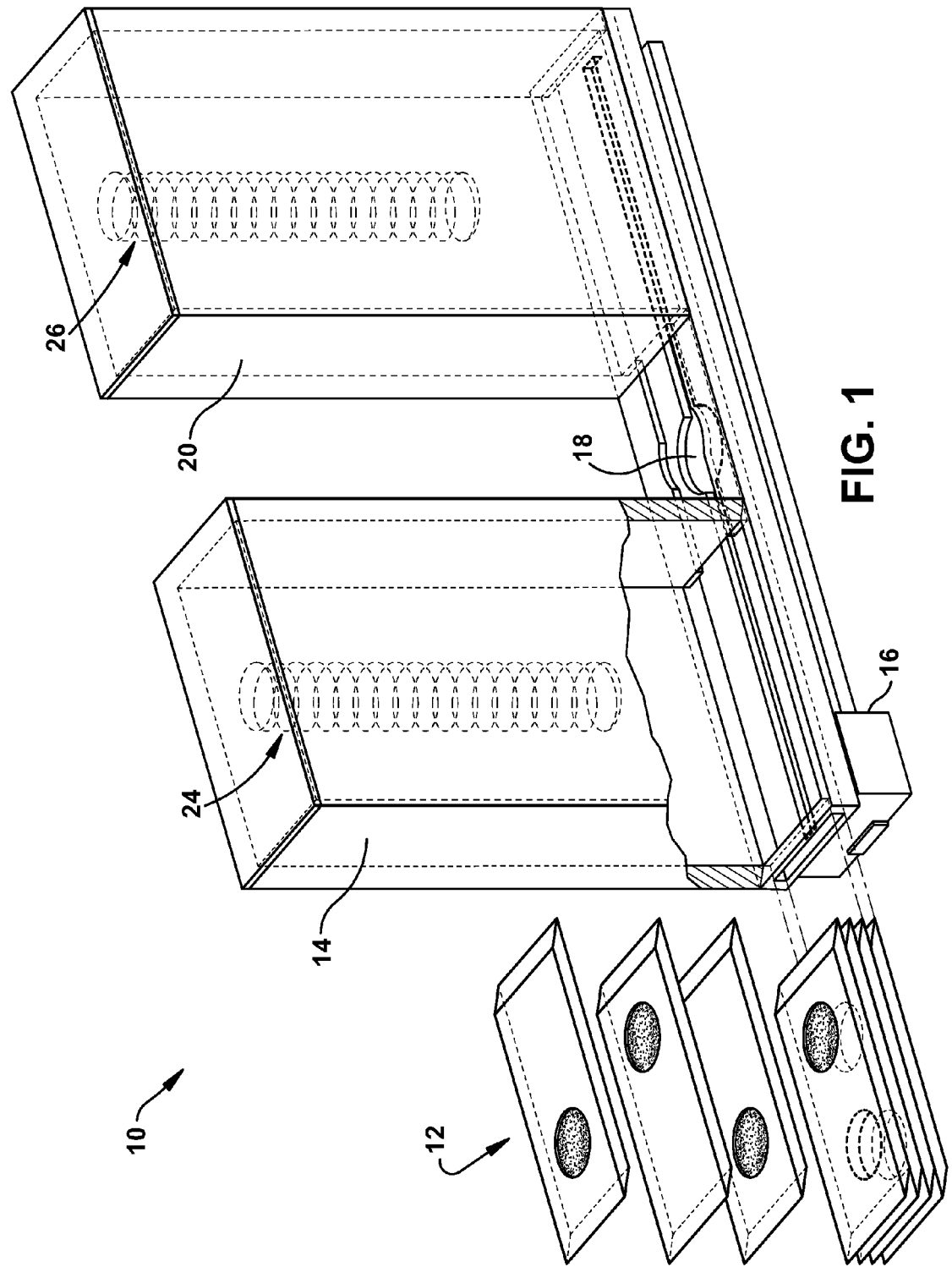
FIG. 1 illustrates a system for automated collection of analytes in accordance with an aspect of the present invention.

The present invention relates to automated systems and methods for the collection of analytes. In one aspect of the invention, a sorbent coated screen autosampler is provided. The term autosampler and automated collection system are employed interchangeably in this description and can be deemed as synonymous. The autosampler can be a battery powered automatic sampling system employing a cartridge containing sorbent coated screens (SCS) mounted in beveled rectangular tabs. This approach enables for rapid sampling and analysis. The SCS tabs are designed such that precleaned SCS tabs and exposed SCS tabs are stored in an isolated air tight configuration. The autosampler is designed to remove one SCS tab at a designated time for collecting vapor and particulate samples onto the SCS, then store the exposed SCS in an isolated air tight configuration that is amenable to automatic analysis using an atmospheric ionization technique.

The autosampler provides a format (sorbent coated screens) that is capable of rapidly collecting both vapor and particulate samples. The design of the autosampler allows for isolation of each SCS from both the environment and other SCS' making it possible to correlate both spatial and temporal data to the analytical data from the analysis of the individual SCS. The autosampler provides the ability to have automated sampling for time resolved chemical analysis data of air using SCS. The mechanical design of the auto-sampler as well as the tabs that the screens are mounted in are designed to mate with the recently developed SCS which have considerable advantages over sorbent tubes such as size, back pressure and analytical time. They are designed for use with Atmospheric Ionization Techniques such as DART and DESI, but it may be possible to perform thermal desorption from the SCS media as well. Sorbent substrates are not subject to the limitations of sorbent tubes as their geometry allows near instant ionization and sample transfer to a detector such as a mass spectrometer or ion mobility spectrometer.

In aspect of the invention, the autosampler sampler include two cartridges, one containing precleaned SCS and the second for storing exposed SCS. The SCS is mounted in tabs such that by stacking the tabs each SCS is sealed by the adjacent SCS tabs. This is accomplished by offsetting the SCS channels to different ends of the tab such that when 2 tabs are stacked, the SCS channel of one is covered by the blank face of the other SCS tab. By stacking a number of tabs (e.g., 50) each SCS is sealed by the SCS tab above and below it. The precleaned SCS tab cartridge is loaded into the autosampler on one side and the storage cartridge for exposed SCS tabs on the opposite side. The air sampling region lies between the two cartridges such that to begin sampling, a precleaned SCS tab is pushed, via a linear actuator, out of the precleaned cartridge into the sampling area.

Air sampling is accomplished using a quiet air pump or fan which pulls the air sample trough the SCS. Because the SCS exhibit extremely low pressure drops thereby requiring very little pull to move air through the SCS, it is possible to use something as simple as a computer cooling fan for sample collection. After sampling is completed, the linear actuator loads another precleaned SCS tab into the sampling area and at the same time the exposed SCS tab is pushed into the storage cartridge where it is held in place by a spring in the cartridge such that the SCS is sealed from environmental contamination in the same manner as in the first cartridge. The SCS tabs have beveled ends so that they can be slid into a cartridge already containing SCS tabs easily.

Figure 2:
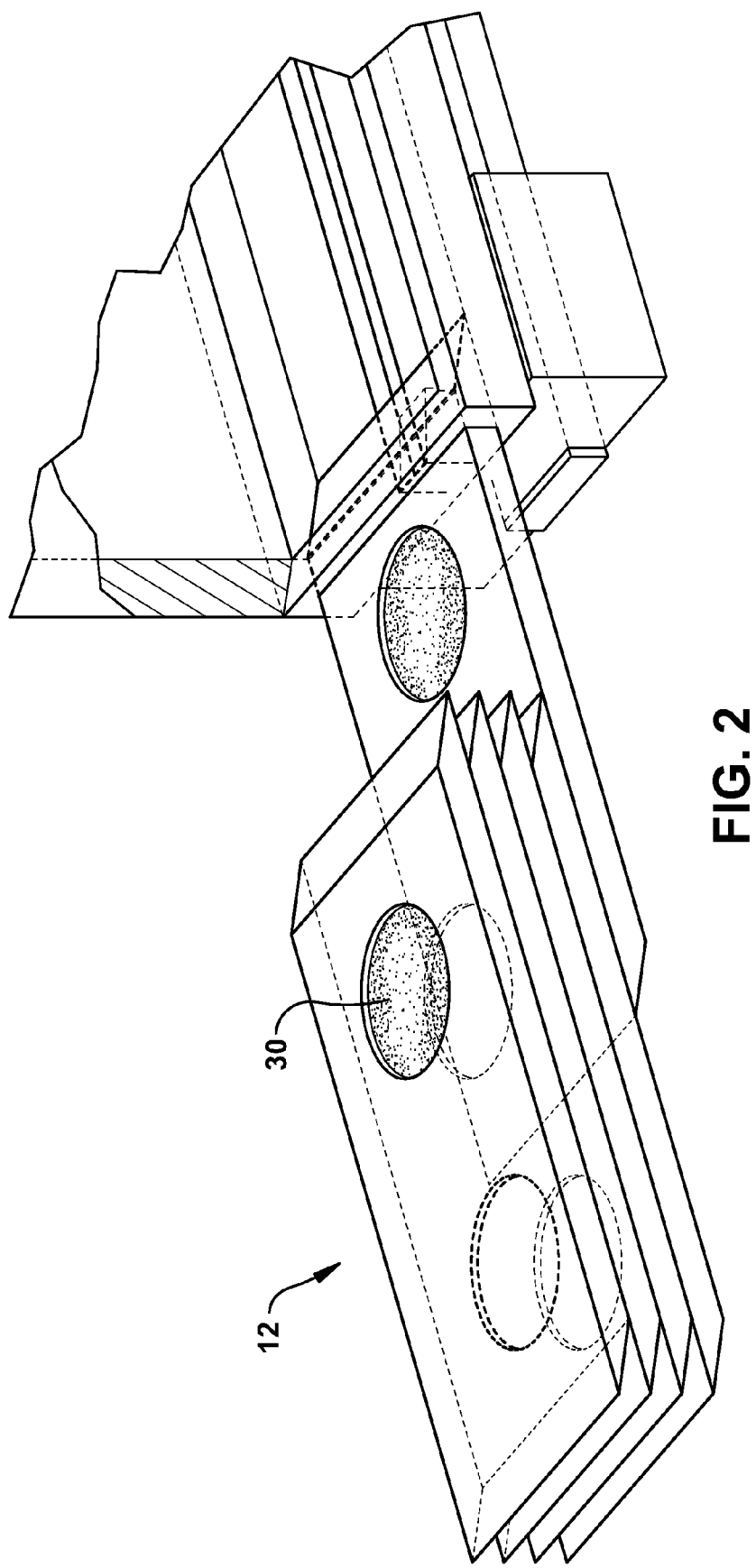
FIG. 2 illustrates a close up view of an alternating stack of SCS tabs in accordance with an aspect of the present invention.

In another aspect of the invention, the autosampler utilizes one cartridge. This cartridge contains precleaned SCS tabs as in the previous approach, however, the cartridge is used to contain both exposed and precleaned SCS tabs. In this system, a SCS tab is pushed into the sampling zone using a linear actuator in the same manner as the previous approach. After sampling, the linear actuator pulls the SCS tab back into its original position in the cartridge. The cartridge is then moved down such that the next precleaned SCS tab is lined up with the linear actuator and sampling zone. The cartridge will have a geared edge which meshes with a gear system on the sampler that rotates in a clockwise direction to move the cartridge down readying another preccleaned SCS tab for sampling. In this manner, the cartridge moves down though the autosampler exposing precleaned SCS tabs then storing the exposed tabs in the same cartridge. Because the SCS channels are offset and the SCS tabs are held in a stack by a spring, the SCS are isolated from each other and the environment once they are in the stack FIG. 1 illustrates a system 10 for automated collection of analytes in accordance with an aspect of the present invention. A stack of SCS tabs 12 are arranged in an alternating stacked configuration. Each SCS tab includes a SCS channel that resides on one end of the SCS tab. The stack 12 of SCS tabs are arranged such that the SCS tabs alternate between tabs having an SCS channel on a first end and tabs having an SCS channel on a second end opposite the first end. This allows for SCS channels to be isolated from each other and the environment when the SCS tabs are arranged in an alternating stacked configuration. FIG. 2 illustrates a close up view of the alternating stack of SCS tabs 12 such that a SCS channel is located on a first end on a first SCS tab with a closed end or channel on a second end of the first SCS tab. A second SCS tab overlies the first SCS tab and includes a closed end on the first end of the second SCS tab with a SCS channel residing on a second end of the second SCS tab, such that the closed end of the second SCS tab seals the SCS channel on the first end of the first SCS tab.

The alternating stack of SCS tabs 12 are loaded into a screen supply cartridge 14 and held down by a cover (not shown) that includes a spring 24 that holds down the alternating stack of SCS tabs 12. A first SCS tab is moved into a sample region 18 by a linear rail stepper motor 16. An air source (not shown) provides a supply of air containing a given analyte through a thin adsorptive material layer disposed in the SCS channel of the first SCS tab. Alternatively, the air source can be a vacuum that pulls the analyte through the thin adsorptive material layer. A second new SCS tab is then moved into place of the sample region 18 and the first SCS tab is moved into a post sample storage cartridge 20. An air source (not shown) provides a supply of air containing a given analyte through a thin adsorptive material layer of the SCS channel of the second SCS tab. A third new SCS tab is then moved into place of the sample region 18 and the second SCS tab is moved into the post sample storage cartridge 20.

Since each SCS tab includes a beveled end, the second SCS tab causes the first SCS tab to move upward in the post sample storage cartridge 20, while the first SCS tab slides under the second SCS tab, such that the SCS channel of the second SCS tab is isolated from the SCS channel of the first SCS tab. This process can be repeated until the post sample storage cartridge 20 is filled. The post sample storage cartridge 20 can be covered with a cap (not shown) that includes a spring 26 for spring loading of the SCS tabs. The post sample storage cartridge 20 can then be removed from the autosampler 10 for shipment to a lab and be replaced with a new empty post sample storage cartridge. Additionally, a new supply of clean SCS tabs can be provided to a screen supply stack cartridge 14, such that the autosampling process can be repeated.

Figure 3:
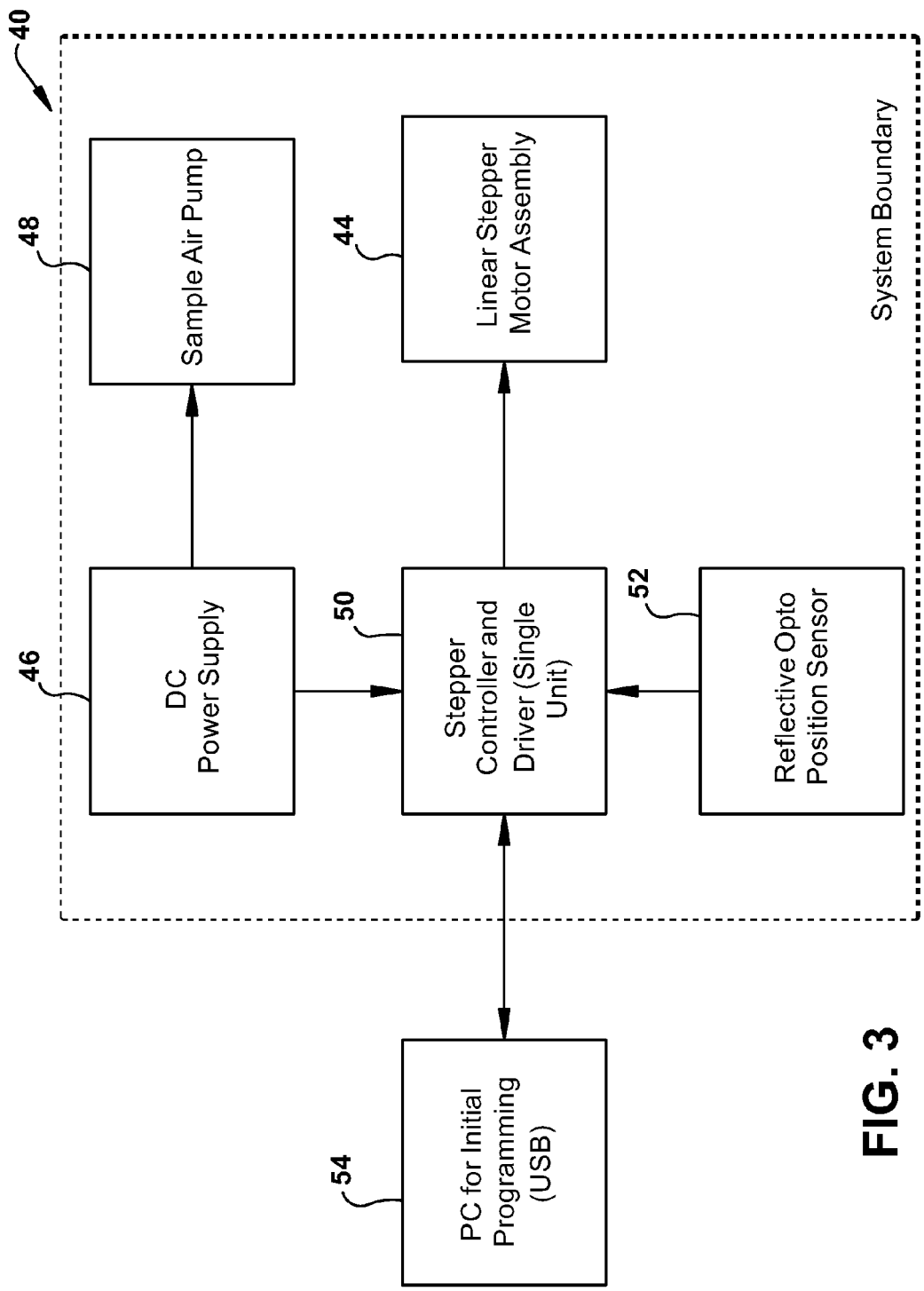
FIG. 3 illustrates a schematic block diagram of an autosampler system in accordance with an aspect of the present invention.

FIG. 3 illustrates a schematic block diagram of an autosampler system 40 in accordance with an aspect of the present invention. The autosampler system 40 includes a stepper controller and driver unit 50 configured to control and drive a linear stepper motor assembly 44 that drives the SCS tabs from the screen supply cartridge to the sample region and then to the post sample storage cartridge. The stepper controller and driver unit 50 is powered by a DC power supply 46 which also provided power to a sample air pump 48. The stepper controller and driver unit 50 can be initially programmed by a personal computer 54 via a USB port. A reflective opto-position sensor 52 provides feedback to the stepper controller and driver unit 50 to inform the stepper controller and driver unit 50 when a SCS tab is in proper placement on the sample region for sampling.

FIG. 4 illustrates a top view of an SCS tab 60 in accordance with an aspect of the invention. The SCS tab 60 includes a generally rectangular central portion 62 with a first beveled end 64 on a first end and a second beveled end 70 on a second end. The first beveled end 64 and the second beveled end 70 are also on opposite faces of the SCS tab 60. A SCS channel 66 with a sorbent material resides on the first end of the SCS tab and a closed channel 68 resides on the second end of the SCS tab 60. In this manner a single SCS tab can be fabricated and flipped over to provide an alternating stack of tabs with alternating tabs having SCS channels on opposite ends. The SCS tab 60 can have a width of about 15 mm with a thickness of about 3 mm. The SCS tab is designed in such a way as to fit into a cartridge 80 with the SCS channels offset as illustrated in FIG. 5. A cover 81 that includes a spring 82 in the cartridge keeps pressure on the stack effectively holding down and sealing each SCS channel from the environment and from other SCS channels.

Figure 8:
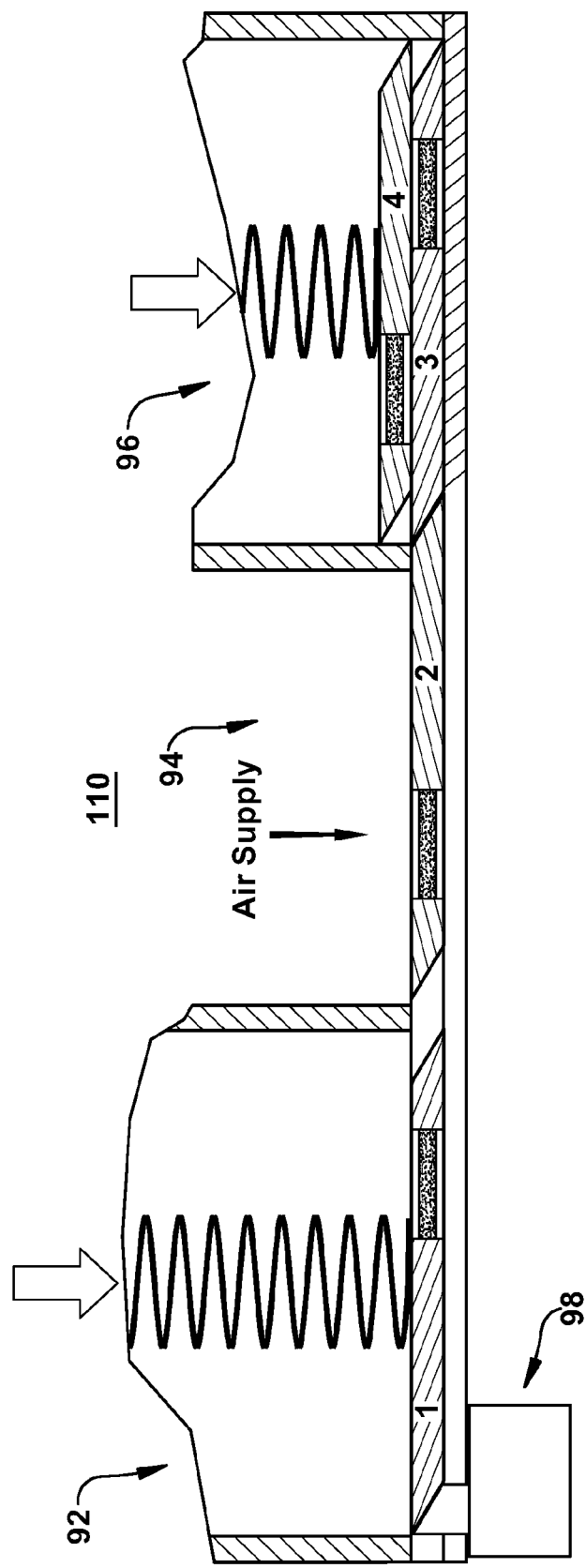
FIG. 8 illustrates operation of the SCS autosampler during a third stage of operation in accordance with an aspect of the present invention.

In view of the foregoing structural and functional features described above, a methodology in accordance with various aspects of the present invention will be better appreciated with reference to FIGS. 6-8. FIGS. 6-8 illustrate operation of the SCS autosampler during different stages of operation. FIG. 6 illustrates operation of the SCS autosampler during a first stage 90 of operation in accordance with an aspect of the present invention. In the first stage 90, a first clean SCS tab (1) and a second SCS tab (2) reside in a clean cartridge 92. A third SCS tab (3) resides on a sampling region 94, while a fourth SCS tab (4) is done sampling and has been stored in the exposed sampler cartridge 96. The clean SCS tabs are mounted in the clean cartridge 92 which is airtight and provided with a spring that provides tension to seal the individual SCS components from the environment and each other. The system utilizes a linear actuator 98 to move precleaned SCS tabs from the clean cartridge 92 into the sampling region 94 as well as moving exposed SCS tabs into the exposed sampler cartridge 96.

FIG. 7 illustrates operation of the SCS autosampler during a second stage 100 of operation in accordance with an aspect of the present invention. In the second stage 100, the linear actuator 98 moves the second SCS tab (2) from the clean cartridge 92 into the sampling position. At the same time the exposed third SCS tab (3) is moved into the exposed sampler cartridge 96. The beveled edges of the exposed third SCS tab (3) force up the previously exposed fourth SCS tab (4). FIG. 8 illustrates operation of the SCS autosampler during a third stage 110 of operation in accordance with an aspect of the present invention. In the third stage 110, the linear actuator 98 moves the third SCS tab (3), such that the third SCS tab (3) is fully inserted into the exposed sampler cartridge 96. Due to the offset of the SCS channels in the tab bodies, each SCS channel is isolated from the environment as well as other exposed SCS channels. A spring in the exposed sampler cartridge 96 retains pressure on the SCS tab to hold a tight seal. The second precleaned SCS tab (2) has been fully placed into the sampling region 100. The precleaned first SCS tab (1) is in the ready position for loading into the sampling region 94 after the second SCS tab (2) completes its collection.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. An automated system for collecting analytes, the system comprising:
    a screen supply cartridge for holding a stack of clean tabs including sorbent coated screens (SCS) residing in SCS channels, with SCS channels offset from the SCS channels of adjacent tabs to isolate the SCS channels from one another and the environment;
    an air source that provides an analyte to be adsorbed by an SCS channel of a respective tab at a sampling region; and
    a linear actuator that moves a given clean tab into the sampling region for exposing the SCS channel of the given clean tab to the analyte and providing a given exposed tab.

2. The system of claim 1, wherein the linear actuator moves the given exposed tab from the sampling region into a post sampling cartridge.

3. The system of claim 2, wherein each of the tabs have beveled ends, such that the beveled end of a clean tab moves the given exposed tab from the sampling region into a post sampling cartridge and the given exposed tab pushes a prior exposed tab up or down the post sampling cartridge to create a stack of exposed tabs in the post sampling cartridge arranged such that SCS tabs directly above and below a given SCS tab include SCS channels offset from the SCS channel of the given SCS tab to isolate the SCS channels from one another and the environment.

4. The system of claim 3, wherein the post sampling cartridge and the screen supply cartridge have spring loaded tops covering the respective cartridges.

5. The system of claim 1, wherein a linear motor moves the given exposed tab back into the screen supply cartridge.

6. The system of claim 5, wherein each of the tabs have beveled ends, such that the beveled end of an exposed tab pushes a prior exposed tab or clean tab up or down the screen supply cartridge to create a stack of exposed tabs arranged such that SCS tabs directly above and below a given SCS tab include SCS channels offset from the SCS channel of the given SCS tab to isolate the SCS channels from one another and the environment.

7. The system of claim 6, wherein the screen supply cartridge has a spring loaded top.

8. The system of claim 1, wherein the linear actuator is a linear stepper motor.

9. The system of claim 1, wherein the air source is a quiet air pump or fan.

10. An automated system for collecting analytes, the system comprising:
    a screen supply cartridge for holding a stack of clean tabs including sorbent coated screens (SCS) residing in SCS channels, the stack of tabs being arranged such that SCS tabs alternate between first tabs having an SCS channel on a first end and a closed end on a second end and second tabs having SCS channels on a second end and closed ends on a first end, such that an SCS channel of a given tab aligns with a closed end of adjacent tabs to isolate the SCS channels from one another and the environment;
    an air source that provides an analyte to be adsorbed by an SCS channel of a respective tab at a sampling region; and
    a linear actuator that moves a given clean tab into the sampling region for exposing the SCS channel of the given clean tab to the analyte and providing a given exposed tab.

11. The system of claim 10, wherein the linear actuator moves the given exposed tab into a post sampling cartridge.

12. The system of claim 11, wherein each of the tabs have beveled ends, such that the beveled end of an exposed tab pushes a prior exposed tab up or down the post sampling cartridge to create a stack of exposed tabs in the post sampling cartridge arranged such that SCS tabs alternate between first tabs having an SCS channel on a first end and a closed end on a second end and second tabs having SCS channels on a second end and closed ends on a first end, such that an SCS channel of a given tab aligns with a closed end of adjacent tabs to isolate the SCS channels from one another and the environment.

13. The system of claim 10, wherein a linear motor moves the given exposed tab back into the screen supply cartridge, such that the cartridge has a geared edge which meshes with a gear system on the sampler to move the cartridge down or up readying another clean SCS tab for sampling.

14. The system of claim 13, wherein each of the tabs have beveled ends, such that the beveled end of an exposed tab pushes a prior exposed tab or clean tabs up or down the screen supply cartridge to create a stack of exposed tabs arranged such that SCS tabs directly above and below a given SCS tab tabs alternate between first tabs having an SCS channel on a first end and a closed end on a second end and tabs having SCS channels on a second end and closed ends on a first end, such that an SCS channel on a given tab align with a closed end of a tab directly above and/or below the given tab to isolate the SCS channels from one another and the environment.

15. A method for collecting analytes, the method comprising:
providing a screen supply cartridge for holding a stack of clean tabs including sorbent coated screens (SCS) residing in SCS channels, the stack of tabs being arranged such that SCS tabs directly above and below a given SCS tab include SCS channels offset from the SCS channel of the given tab and closed ends of the SCS tabs are aligned with SCS channels of SCS tabs directly above and/or below respective SCS tabs to isolate the SCS channels from one another and the environment;
loading a given clean tab from the screen into a sampling region for exposing the SCS channel of the given clean tab to an analyte;
pulling the analyte to be adsorbed through the SCS channel of the clean tab employing an air source to provide a given exposed tab.

16. The method of claim 15, further comprising moving the given exposed tab into a post sampling cartridge.

17. The method of claim 16, wherein each of the tabs have beveled ends, such that moving a second clean tab into the sampling region moves the given exposed tab into the post sampling cartridge.

18. The method of claim 16, wherein moving the given exposed tab into the post sampling cartridge pushes a prior exposed tab up or down the post sampling cartridge to create a stack of exposed tabs in the post sampling cartridge arranged such that SCS tabs directly above and below a given SCS tab include SCS channels offset from the SCS channel of the given SCS tab to isolate the SCS channels from one another and the environment.

19. The method of claim 15, further comprising moving the given exposed tab from the sampling region back into the screen supply cartridge.

20. The method of claim 19, wherein each of the tabs have beveled ends, such that moving the given exposed tab back into the screen supply cartridge causes the beveled end of an exposed tab pushes a prior exposed tab or clean tab up or down the screen supply cartridge to create a stack of exposed tabs arranged such that SCS tabs directly above and below a given SCS tab include SCS channels offset from the SCS channel of the given SCS tab to isolate the SCS channels from one another and the environment.

* * * * *